United States Patent [19]

Atasoy et al.

[11] 4,125,602

[45] Nov. 14, 1978

[54] PROCESS FOR THE PRODUCTION OF IODOPHORS

[75] Inventors: Kaya Atasoy, Munchenstein; Karl F. Weckwarth, Basel; Walter Reinhardt, Pratteln, all of Switzerland

[73] Assignee: Ciba-Geigy Corporation, Ardsley, N.Y.

[21] Appl. No.: 835,075

[22] Filed: Sep. 20, 1977

Related U.S. Application Data

[63] Continuation-in-part of Ser. No. 635,028, Nov. 25, 1975, abandoned.

[30] Foreign Application Priority Data

Dec. 2, 1974 [CH] Switzerland .................... 15955/74

[51] Int. Cl.$^2$ .................... A01N 11/00; A61K 31/79; A61K 33/18; A61L 13/00
[52] U.S. Cl. .................................... 424/80; 424/150
[58] Field of Search ................... 424/80, 150

[56] References Cited

U.S. PATENT DOCUMENTS

| | | | |
|---|---|---|---|
| 2,706,701 | 4/1955 | Beller et al. | 424/80 |
| 2,739,922 | 3/1956 | Shelanski | 424/80 |
| 2,987,505 | 6/1961 | Werner | 424/150 |
| 3,028,300 | 4/1962 | Cantor et al. | 424/80 |
| 3,898,326 | 8/1975 | Cantor et al. | 424/80 |
| 4,038,476 | 7/1977 | Atasoy et al. | 424/80 |

FOREIGN PATENT DOCUMENTS

| | | | |
|---|---|---|---|
| 617,083 | 3/1961 | Canada | 424/80 |
| 1,073,745 | 1/1960 | Fed. Rep. of Germany | 424/80 |

Primary Examiner—Albert T. Meyers
Assistant Examiner—D. W. Robinson
Attorney, Agent, or Firm—Frederick H. Rabin

[57] ABSTRACT

Preparation of iodophor granules of practically uniform particle size consisting of poly-N-vinyl-pyrrolidone, iodine and substance releasing iodide ions by combining with uniform thorough mixing (a) a solution and/or colloidal suspension of elementary iodine and a substance releasing iodide ions in a first solvent or solvent mixture, as well as (b) a solution and/or colloidal solution and/or suspension of PVP in a second solvent or solvent mixture which has a surface tension different from that of the first solvent or solvent mixture, and in which PVP is at least partially soluble or wettable, and in which the substances dissolved or suspended in the first solvent or solvent mixture are insoluble or only slightly soluble, and separating and drying the granules formed.

14 Claims, No Drawings

PROCESS FOR THE PRODUCTION OF IODOPHORS

CROSS-REFERENCE TO RELATED APPLICATION

This is a continuation-in-part of application Ser. No. 635,028 filed Nov. 25, 1975, now abandoned.

DETAILED DISCLOSURE

The present invention relates to a novel process for the production of germicidally acting complexes of poly-N-vinylpyrrolidone (PVP) with iodine, the material being in the form of granules of practically uniform particle size, which process comprises producing (a) a solution and/or colloidal suspension of elementary iodine and a substance releasing iodide ions in a first solvent or solvent mixture, as well as (b) a solution and/or colloidal solution and/or suspension of PVP in a second solvent or solvent mixture which has a surface tension different from that of the first solvent or solvent mixture, and in which PVP is at least partially soluble or wettable, and in which the substances dissolved or suspended in the first solvent or solvent mixture are insoluble or only slightly soluble;

combining the solutions or suspensions (a) and (b), with uniform thorough mixing, in small portions to thus form a mixed-phase-system; continuing the thorough mixing of the multiphase mixture; and separating and drying the formed agglomerates containing the iodine/PVP complex and iodide ions.

From the USA Patent Specification No. 3,028,300 there is known a process for producing iodophors, i.e. agents containing iodine bound in complex linkage with PVP. These agents, which are characterised by a high degree of iodine-complexing, are produced by mechanically mixing together a pulverulent mixture of of PVP, elementary iodine and iodide during a period of about 24 hours at room temperature. The degree of iodine-complexing obtained is expressed by the so-called distribution coefficient (DC) (see columns 2 and 3 of the USA Pat. Specification No. 3,028,300). Furthermore, it is known from the Belgian Pat. Spec. No. 814918 that iodophors are produced by starting with a pulverulent spray-dried mixture of PVP and an iodide, and converting this mixture by 2- to 3-hours' mechanical mixing with elementary iodine at room temperature into a iodophor complex, which is a stable, single-phase solid solution of iodide in PVP with homogeneously distributed iodine bound in complex linkage.

Disadvantages of the above described processes, which are based on a mechanical mixing together of the iodophor constituents, are the iodine loss due to evaporation, the undesirable formation of iodide from iodine, and the impossibility of recovering lost iodine. A further disadvantage lies in the long duration of mechanical mixing to effect complexing of the elementary iodine, which applies in particular to the process of the USA Patent Specification No. 3,028,300 mentioned above. The use of spray-dried PVP/iodide preparations as starting material for producing iodophors certainly requires a shorter mixing time, but an appreciable amount of equipment is necessary and the spray-dried products exhibit a fairly wide particle-size distribution with a high proportion of fines. The products hitherto produced in this manner display adequate iodine-complexing, but are largely in the form of pulverulent solids and release more or less a high amount of dust. Moreover the rate of dissolving of such pulverulent preparations is, in consequence of the less favourable wetting property, in many cases too low for modern requirements in industry, a factor resulting in loss of time in the production of solutions or in the necessity for special stirring devices to be used.

In connection with the process according to the present invention, it is pointed out that working procedures to effect the agglomeration and separation of finely divided solid substances of inorganic nature from liquid suspensions or dispersions by the use of various solvent combinations are already known (see Can. J. Chem. Vol. 38 (1960), pages 1911–1916, and USA Patent Specification No. 3,268,071). The application of multiphase systems with solvents of varying miscibility for producing soluble granules from originally finely divided organic substances, such as dyestuffs and foodstuffs, is described in the German 'Offenlegungsschrift' No. 2,412,369. In this process the finely divided or pulverulent substances to be granulated are suspended in a liquid system, and then added, with turbulent stirring, to a second liquid solvent or solvent mixture, with the formation of granules resulting. Disadvantages of the aforementioned processes are that they do not permit of the incorporation of further constituents into the formed granules nor do they permit the processing of true solutions of the substances to be granulated. Also the production of complexes, especially of iodophors, cannot be successfully carried out by means of these known processes.

Compared with the hitherto known working procedures for the production of iodophors, the process of the present invention is characterised by simplicity, by a low expenditure for equipment, by high economy in operation and, in particular, by the fact that by this process there are obtained for the first time iodophors in the form of free-flowing, non-dusty and readily water-soluble granules of practically uniform particle size and of homogeneous composition. The iodophor granules obtained possess similar advantageous chemical and physicochemical properties to those of the iodophor products according to the initially mentioned Belgian Patent Specification No. 814,918. Of particular advantage is that the present process can be performed in a very short time, generally within 15 to 30 minutes, and moreover without the use of expensive equipment, such as spray dryers or corrosion-resistant, closed mixing devices. A further advantage of the process of the invention is that it is not only suitable for batch operation but that it is also particularly suitable for continuous operation.

The yields of iodophor granulate which are attainable by the process of the invention can be up to 100 per cent by weight, relative to the total weight of the constituents used. In general, yields of between 75 and 100 per cent by weight are obtained, the exact percentage depending on various parameters such as concentration of reactants in the solvents, rate of addition, temperature, duration and speed of stirring, etc. By routine experimentation known to persons skilled in the art, various sets of parameters can be developed which will give predictable yields. The unreacted portions of iodine, iodide ($I^{\ominus}$) and PVP can, in addition to the solvents, be easily recovered from the liquid residual mixtures. Or the residual mixtures in the case of continuous operation are fed back in a circulation system, separated as required from each other and the constituents are then re-introduced into the circulation system of the process.

In the case of the present process it is necessary, depending on the type of solvent employed and on the temperature, to provide the mixing vessel with reflux devices. The thorough mixing of the multiphase mixture and the addition of the solution or suspension (a) to the solution or suspension (b) — or inversely — is performed in small portions, e.g. by the dropwise addition, or injection through a nozzle system, of the portions added. The rate of addition should be adjusted to ensure that the formation of the desired agglomerates proceeds continuously. In the thorough mixing of the multiphase system, e.g. by stirring, care must be taken to avoid the occurrence of shearing forces and of turbulence in the mixture. Otherwise the formation of agglomerates would be prevented or impaired.

The agglomerates are separated from the liquid multiphase system in a manner known per se, e.g. by filtration, and dried at a temperature at which no lossess of iodine through evaporation occur.

The process of the invention is preferably performed at room temperature. It has however been shown that it is possible to operate at 0° C and below, as well as up to a temperature of 50° C and above. The possibility of being able to operate within a fairly large temperature range depends largely on the nature of the employed solvent.

Sodium iodide or potassium iodide are preferred as substances releasing iodide ions. It is however possible to work with all water-soluble substances releasing iodide ions, including the iodides of potassium, lithium, magnesium, calcium, aluminium, ammonium, amines and quaternary ammonium, as well as hydriodic acid.

As solvents suitable for the process of the present invention, there may be mentioned representatives having solvent properties of the following classes of solvents: alcohols, esters, carboxylic acids, ethers, ketones, ketone alcohols, amides, lactams, amines, hydrocarbons, halogenated hydrocarbons and water. The following are, for example, suitable:

2-diethylaminoethanol, diacetone alcohol, propylene glycol, butanol-2, methanol, trichlorofluoromethane, dichlorodifluoromethane and other perhalogenated methanes or ethanes where the halogen atoms are fluorine and chlorine, cyclohexane, chloroform, ethyl acetate, cyclohexanol, ethyl formates, citric acid triethyl ester, ethylene glycol mono-n-butyl ester, butanol-1, benzoic acid benzyl ester, benzyl alcohol, ethylene glycol monoethyl ether, ethanolamine, ethylene glycol monomethyl ether, ethylene glycol, 2-acetoxy-ethanol, ethylenediamine hydrate, diethylacetamide, diethylcarbamate, N,N-dimethylformamide, 1,2-diethoxyethane, dioctylphthalate, diethylamine, dioxane, dimethylsulphoxide, N,N-dimethylacetamide, diisopropyl ether, dipentenes, n-hexane, hexadecyl alcohol, acetic acid propyl ester, isopropyl chloride, isopropyl palmitate, n-hydroxy-ethyl-lactamide, methanesulphonic acid, methacrylic acid, mesitylene, methacrylic acid 2-hydroxyethyl ester, morpholine, n-methylpyrrolidone, aliphatic hydrocarbons, lactic acid ethyl ester, salicylic acid methyl ester, phthalic acid dibutyl ester, phenylethyl alcohol, myristinic acid isopropyl ester, carbon tetrachloride, propylenecarbonate, propargyl alcohol, salicylic acid ethyl ester, 2,2-dimethyl-4-oxymethyl-1,3-dioxalane, phthalic acid diethyl ester, 2-propyloxyethanol or palmitic acid isopropyl ester.

The choice of solvents or solvent mixtures has to be made on the basis of the requirement that the second solvent or solvent mixture has not to be capable of dissolving, in any significant amount, elementary iodine or the substance releasing iodide ions, such as alkali iodides. On the other hand, PVP has to become dissolved, colloidally dissolved, partially dissolved or at least so well wetted by the second solvent or solvent mixture that a PVP suspension can readily form. The first solvent or solvent mixture should as far as possible completely dissolve the elementary iodine and the substance releasing iodide ions. The process can however also be performed when the elementary iodine and/or the substance releasing iodide ions are present as colloidal solutions in the first solvent or solvent mixture. In order to obtain homogeneous agglomerates or granules, it is essential that the first solvent or solvent mixture have a value of surface tension that is different from that of the second solvent or solvent mixture.

The following solvents are preferably used as the first solvent or solvent mixture: aliphatic alcohols, especially those having 1–4 carbon atoms, aliphatic ketones, particularly those having 3–9 carbon atoms, alkylacetates, especially those having 2–4 carbon atoms in the alkyl group.

The following solvents are preferably used as the second solvent or solvent mixture: halogenated hydrocarbons having 1–4 carbon atoms, especially perhalogenated hydrocarbons having 1 or 2 carbon atoms, such as $CCl_4$, $CFCl_3$, $CF_3Cl$, $C_2F_3Cl_3$ or $C_2F_4Cl_2$; liquid hydrocarbons having 5–14 carbon atoms, such as n-hexane, cyclohexane, methylcyclohexane, octane, decane, dipentene, dodecane or tetradecane; aliphatic ethers having 2–8 carbon atoms, such as diethyl ether, tetrahydrofuran or diisopropyl ether; phthalic acid esters such as dibutylphthalate; and trialkylamines such as triethylamine.

With various solvent combinations it can be advantageous if the first solvent or solvent mixture contains an addition of water. The amount of water can be up to 20 per cent by weight, preferably 0.5 – 10 per cent by weight, relative to the first solvent or solvent mixture.

As PVP-constituent it is possible to use, without limitation, all available forms which lie within the molecular-weight range of between about 5000 and 750,000 preferably between 20,000 and 40,000, including the Types K-15, K-30 and K-90 (for the significance of the K-values with regard to molecular weight and viscosity see US Patent Specification No. 2,706,701).

As already mentioned, the present invention is characterised by high yields with respect to the iodine and iodide used. It is therefore possible without difficulty to determine beforehand the desired composition of the final products, i.e. of the iodophor granules, with regard to the amounts of iodide and of iodine bound in complex linkage contained in the final products, by the appropriate selection of the amounts of PVP, iodine and iodide in the starting solutions or starting mixtures. In general, the amounts of iodine and of the substance releasing iodide is so arranged that iodophor granules are obtained which have a weight ratio of iodide ions ($I^\ominus$) to iodine of 0.2 : 1 to 5 : 1, preferably 0.5 : 1 to 3 : 1; and a weight ratio of PVP to iodine of 1 : 1 to 20 : 1, preferably 3 : 1 to 5 : 1.

The process of the invention yields, with established working procedures, iodophor granules of practically uniform particle size.

The average particle size obtainable by the process of this invention ranges from about 10 μ to about 3 mm, most frequently from 50 μ to 500 μ. The size of the particles is a function of the solvent used, the rate of addition, temperature, batch size, reaction time, duration and speed of stirring, and drying method. These various parameters can be varied according to routine methods and a set of process conditions can be developed to yield iodophor granules having the desired average particle size. An important advantage in the process of this invention is that, regardless of the average particle size obtained (within the above mentioned limits), the particles will be of practically uniform particle size. The variation between the smallest and the largest particles will be no greater than about 20 % from the average particle size.

This invention is illustrated by following specific examples which are exemplary only and are not intended to be regarded as limitations.

EXAMPLE 1

A first mixture consisting of a solution of 8 g of elementary iodine and 12 g of 57% (by weight) hydriodic acid (HI) in 50 ml of ethyl acetate is added dropwise (rate of addition = 5 ml/min.) at room temperature with stirring (200 r.p.m.), and with the use of a reflux device, to a second mixture consisting of a suspension of 25 g of PVP K-30 in 200 ml of cyclohexane. There are formed on the multiphase mixture floating brown agglomerates, which are filtered off by suction and dried for 1.5 hours at 60° C in a vacuum drying chamber. The free-flowing brown iodophor granules thus obtained have a content of available iodine of 18.9 per cent by weight and exhibit a very high degree of iodine-complexing as well as having good stability.

EXAMPLE 2

The process of Example 1 is repeated with the modification that the first mixture consists of a solution of 6 g of elementary iodine and 12.5 g of sodium iodide in 12.5 g of 96% ethanol and 50 ml of isobutylacetate, and the second mixture consists of a suspension of 25 g of PVP K-30 in 200 ml of cyclohexane. The content of available iodine in the iodophor granules obtained is 6.3 per cent by weight.

EXAMPLE 3

The process of Example 1 is repeated with the modification that the first mixture consists of a solution of 6 g of elementary iodine and 12.5 g of sodium iodide in 12.5 g of 96% ethanol and 50 ml of acetone, and the second mixture consists of a suspension of 25 g of PVP K-30 in 200 ml of $C_2F_3Cl_3$. The amount of available iodine in the iodophor granules obtained is 9.9 per cent by weight.

EXAMPLE 4

The process of Example 1 is repeated with the modification tht the first mixture consists of a solution of 6 g of elementary iodine and 12.5 g of sodium iodide in 12.5% of 96% ethanol and 50 ml of ethyl acetate, and the second mixture consists of a suspension of 25 g of PVP K-30 in 200 ml of n-hexane. The content of available iodine in the iodophor granules obtained is 10.3 per cent by weight.

EXAMPLE 5

The process of Example 1 is repeated with the modification that the first mixture consists of a solution of 2.25 g of elementary iodine and 2.25 g of potassium iodide in 2.25 g of water, 2.25 g of 96% ethanol and 18.75 ml of ethyl acetate. The content of available iodine in the granules produced is 6.1 per cent by weight.

EXAMPLE 6

The process of Example 1 is repeated with the modification that the first mixture consists of a solution of 5 g of elementary iodine and 5 g of sodium iodide in 2 g of 96% ethanol, 1 g of water and 30 ml of acetone, and the second mixture consists of a colloidal solution or suspension of 20 g of PVP K-30 in 200 ml of tetrahydrofuran. The content of available iodine in the granules obtained is 5 per cent by weight.

We claim:

1. A process for the production of germicidal complexes of poly-N-vinylpyrrolidone (PVP) with iodine, in the form of granules having a particle size of 10μ - 3 mm said granules having weight ratio of iodide ions to iodine of from 0.2:1 to 5:1 and a weight ratio of PVP to iodine of from 1:1 to 20:1, which process comprises the steps of:
   (a) producing a solution or colloidal suspension of (i) elementary iodine and (ii) hydriodic acid or a salt releasing iodide ions in a first solvent or solvent mixture,
   (b) producing a solution or colloidal suspension of PVP in a second solvent or solvent mixture (i) which has a surface tension different from the surface tension of the first solvent or solvent mixture, (ii) in which PVP is at least partially soluble or wettable, and (iii) in which the iodine and the salt dissolved or suspended in the first solvent or solvent mixture are insoluble or only slightly soluble;
   (c) combining the solutions or suspensions (a) and (b), with uniform thorough mixing, in small portions to form a mixed-phase system;
   (d) continuing the thorough mixing for sufficient time to form a multiphase mixture with floating agglomerates containing iodine/PVP complex and iodide ions, and
   (e) separating and drying said agglomerates.

2. Process according to claim 1 wherein the thorough mixing is effected by stirring and in such a manner that in the mixture there occur essentially no shearing forces and no turbulence.

3. Process according to claim 1 which is performed at room temperature.

4. Process according to claim 1 wherein the substance releasing iodide ions is hydriodic acid, ammonium iodide or an alkali iodide.

5. Process according to claim 1 in which the substance is sodium iodide or aluminium iodide.

6. Process according to claim 1 wherein there are used, as the first solvent or solvent mixture, water, aliphatic alcohols having 1–4 carbon atoms, or aliphatic ketones having 3–9 carbon atoms, or mixtures thereof.

7. Process according to claim 1 wherein there are used, as the second solvent or solvent mixture, hydrocarbons or halogenated hydrocarbons having 1–4 carbon atoms, or mixtures thereof.

8. Process according to claim 7 in which the solvent or solvent mixture is perhalogenated hydrocarbons having 1 or 2 carbon atoms.

9. Process according to claim 6 wherein the first solvent or solvent mixture contains water in an amount up to 20% by weight.

10. Process according to claim 9 in which the water is present in an amount of from 0.5 to 10% by weight.

11. Process according to claim 1 wherein there is used PVP having a molecular weight in the range of 5,000 - 750,000.

12. Process according to claim 11 in which the molecular weight of the PVP is 20,000–40,000.

13. Process according to claim 1 wherein there are obtained granules having a weight ratio of iodide ions to iodine of 0.5 : 1 to 3 : 1; and a weight ratio of PVP to iodine of 3:1 to 5:1.

14. Process according to claim 1 in which the granules have a particle size of 50-500 $\mu$.

* * * * *